United States Patent [19]
Ehnstrom

[11] 3,940,492
[45] Feb. 24, 1976

[54] CONTINUOUS FERMENTATION PROCESS

[75] Inventor: Lars Karl Johan Ehnstrom, Tullinge, Sweden

[73] Assignee: Alfa-Laval AB, Tumba, Sweden

[22] Filed: June 25, 1974

[21] Appl. No.: 483,007

[30] Foreign Application Priority Data
July 9, 1973 Sweden .............................. 7309617

[52] U.S. Cl. ..................... 426/16; 195/82; 195/115
[51] Int. Cl.² .................... C12C 11/04; C12C 11/08
[58] Field of Search ................... 426/28, 29, 30, 16; 195/17, 82, 115

[56] References Cited
UNITED STATES PATENTS

| | | | |
|---|---|---|---|
| 2,726,957 | 12/1955 | Kunz | 426/29 |
| 3,627,544 | 12/1971 | Bosewitz et al. | 426/29 |
| 3,746,550 | 7/1973 | Ehnstrom | 195/17 X |

*Primary Examiner*—A. Louis Monacell
*Assistant Examiner*—R. B. Penland
*Attorney, Agent, or Firm*—Cyrus S. Hapgood

[57] ABSTRACT

Wort is continuously supplied to a circuit including an elongated closed channel and through which microorganisms are fed. After fermentation has taken place in the circuit, the mixture of wort and microorganisms is centrifuged to separate it into fermented wort, a living cell mass and impurities, these three components being separately discharged from the centrifuge. The separate discharges of fermented wort and living cell mass are continuous, and the latter discharge includes an excess of living cells formed in the circuit, an amount of cell mass corresponding to this excess being discharged from the circuit.

8 Claims, 1 Drawing Figure

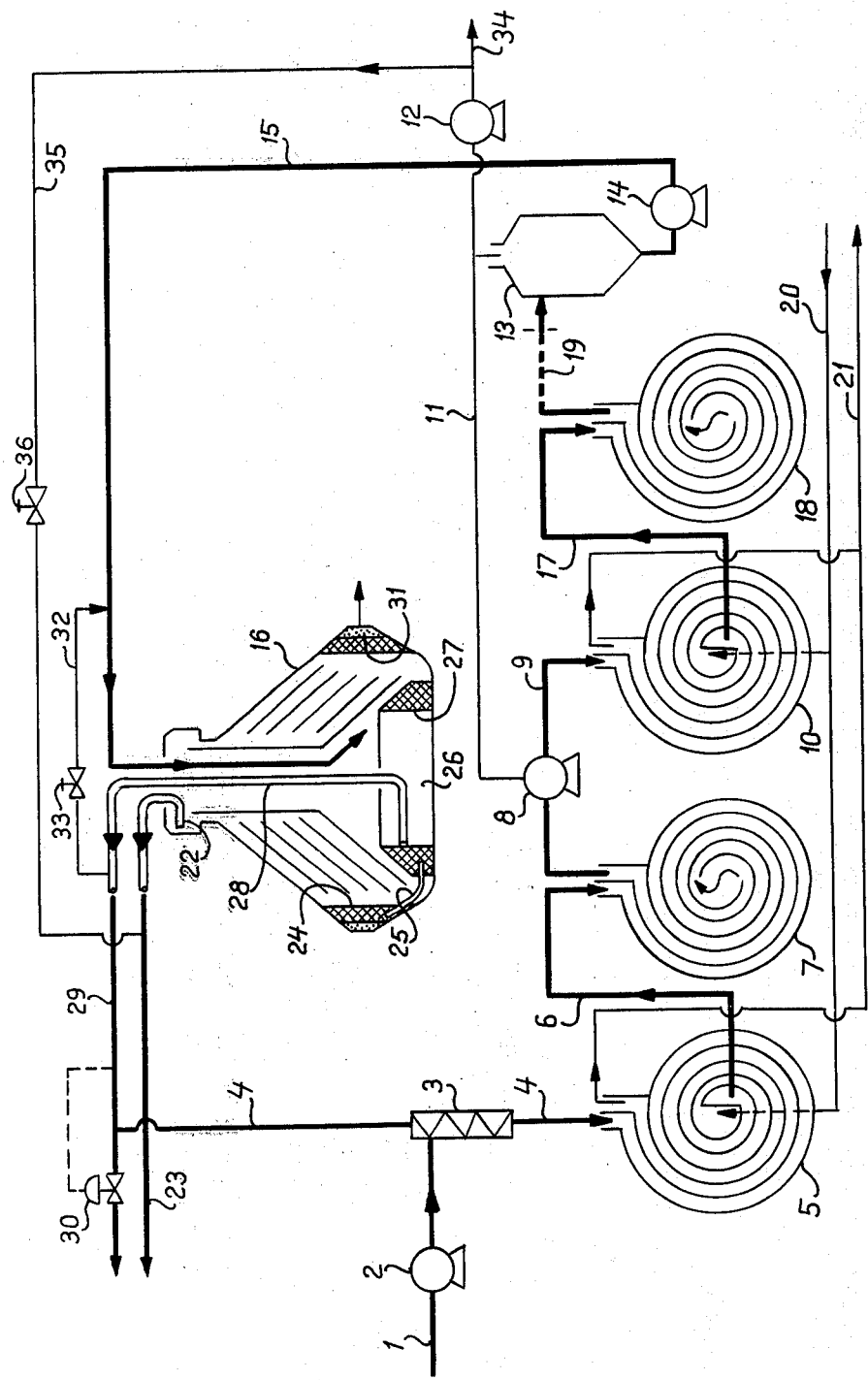

CONTINUOUS FERMENTATION PROCESS

The present invention relates to a method for carrying out continuous fermentation in a wort or other substrate, microorganisms being fed in a circuit which includes an elongated, closed channel and to which wort is continuously supplied. An advantage of this kind of method is the fact that the concentration of cell mass (micro-organisms) in the wort can be kept high during the fermentation course, which circumstance leads to a desirably high fermentation velocity. However, it has proved that the fermentation process ceases after a certain period of operation, and for this reason the operation must be interrupted and the plant must be emptied and cleaned.

The present invention has for its principal object to improve the above-mentioned prior method so that no operating interruptions will be necessary for the continuation of the fermentation process.

According to the invention, the problem is solved by centrifugally separating the mixture of wort and cell mass, after fermentation has taken place in the circuit, into three components, namely, fermented wort, living cell mass and impurities, the fermented wort, and impurities and the formed excess of living cell mass being continuously discharged from the centrifuge. The fermentation process can thus be continued for practically an unlimited long time without interruption. The explanation of this is that the impurities, which have proved to consist of dead yeast cells as well as precipitations formed during the fermentation process (mainly proteins), are accumulated in the circuit in the prior method to such a concentration that their presence stops the fermentation process. The reason for this accumulation is the fact that when producing beer, for example, the discharge of cell mass from the circuit is as small as 1 to 2 percent of the cell mass circulating in the circuit. According to the present invention, it was found that separating the dead cells and the precipitations (= impurities) from the living cell mass is possible because the impurities have a higher density than the living cells.

According to an additional feature of the invention, the centrifuging is carried out so that the living cell mass discharged from the centrifuge has a dry substance content of at least 10 percent by weight. The advantage of this is that it is possible to maintain a high cell concentration and consequently a low flow velocity in the circuit without any trouble due to sedimentation in the channels of the plant. In this way the plant can be made more compact, and at the same time the mixture of wort and cell mass can pass through the closed channel as a coherent plug without any risk of wort parts with different degree of fermentation being mixed.

Furthermore, according to the invention the cell growth in the circuit can be controlled by a controlled supply of oxygen, as in the form of air, to the living cell mass which is discharged from the centrifuge. More exactly, this takes place by means of a paring device which is caused to discharge a controlled mixture of oxygen-containing gas and living cell mass from the centrifuge. By means of this control of the oxygen supply, it is possible to effect an optimum production of the product which is to be produced by the method, such as beer or yeast. The control is effected by controlled throttling of the outlet of the paring device. Thus, a controlled covering of the opening of the paring device, and consequently a control of the ratio of gas to cell mass in the mixture discharged by the paring device, are obtained. At the same time a desired intense admixture of oxygen-containing gas into the cell mass is obtained.

The time of contact between the cell mass and the wort in the circuit can be controlled by control of the flow through the circuit, as by a control of the supply of wort to the circuit. By means of this control, it can be ensured that the content of different fermentable sugars of the wort will be consumed to a satisfactory degree.

Furthermore, according to the invention the temperature can be controlled by indirect heat exchange to different levels in different parts of the closed channel in accordance with a desired temperature program. Thus, it is desirable that the temperature of the fresh wort entering the circuit be rapidly increased to such a temperature that the cells will be active. Thereafter the temperature in the continuation of the channel should be reduced to such a degree that an optimum production of the product is obtained. If the temperature should be too high, especially due to the heat development of the cells themselves, the fermentation course ceases.

If the method is intended for alcohol production, it is suitable to discharge carbonic acid from one or more points of the closed channel for the reason that too high a carbonic acid pressure obstructs continued cell growth and also entails a risk of bursting the parts exposed to the carbonic acid pressure.

By carrying out the fermentation process in an elongated, closed channel, it is possible according to the invention to control the fermentation by additives such as enzymes, acid for the control of the pH value, etc., supplied to different parts of the closed channel.

The closed channel also makes it possible to carry out the fermentation under superatmospheric pressure, so that the fermentation process can be caused to operate faster. The superatmospheric pressure can be effected by the carbonic acid development of the cells and, if this is not sufficient, by pumping in air, for instance, as by means of the paring device previously mentioned. The superatmospheric pressure can be kept different in different parts of the channel.

The invention is described more in detail below, reference being made to the accompanying drawing in which the single illustration is a schematic view of an example of a plant for carrying out the present method.

A pipeline for the supply of fresh wort is shown at 1, and in this pipeline is a pump 2 which feeds a predetermined quantity of wort per unit of time into a mixer 3 of a type operating without movable parts. In this mixer the wort is mixed with a cell mass supplied through a pipeline 4. The mixture of wort and cell mass is fed from the mixer 3 to a helical heat exchanger 5, where the mixture flows in a helical path inwards to a center and in countercurrent to and under indirect heat exchange with a medium which flows through a similar helical path. The mixture flows from said center directly into a pipeline 6 which leads to a helical reactor 7, where the mixture first flows in a helical path inwards to a center and then outwards from this center in another helical path. No heat exchange is effected in the helical reactor 7, which serves as a holding zone for the mixture. The mixture is fed by a pump 8 from the reactor 7 through a pipeline 9 to a helical heat exchanger 10 of the same kind as the heat exchanger 5.

The pump 8 is of a known kind capable of separating foam or gas from the mixture, such as an air excess or carbonic acid; and this gas is discharged via a pipeline 11 by a pump 12, which generates a weak vacuum. Pumps of the same type as the pump 8 are inserted in necessary parts of the closed channel formed by the different helical heat exchangers and the helical reactors. It is possible to use a combination of an expansion vessel and a pump instead of pumps of said kind, as shown by the details 13 and 14. The gas liberated in the expansion vessel 13 is sucked out through the pipeline 11, and the mixture of wort and cell mass is delivered by pump 14 from the bottom of the vessel 13 through a pipeline 15 to a centrifuge 16. The mixture also flows from the helical heat exchanger 10 through a pipeline 17 to a helical reactor 18 of the same kind as the reactor 7. When necessary, additional pairs of a helical heat exchanger and a helical reactor can be connected in series in the pipeline part 19, shown by a broken line.

Since heat is developed by the cell growth, a cooling medium such as cold water is supplied to the helical heat exchangers through a pipeline 20, and the heated cooling medium is discharged through a pipeline 21.

The entering mixture is divided in the centrifuge 16 into spent wort, living cell mass and impurities (dead cells and precipitations). The wort is discharged as the lightest phase by a paring tube 22 and is delivered in its entirety from the plant through a pipeline 23. The living cell mass is a phase of medium weight which collects as the next outermost layer 24 in the sludge space of the centrifuge rotor, and it is led to tubes 25 to a central space 26 where it forms a peripheral layer 27. Living cell mass is discharged from this layer by a paring tube 28 and is mostly led back to the plant through a pipeline 29. Only a small part, corresponding to the quantity of living cell mass newly formed during the circulation through the circuit, is discharged via a valve 30, which keeps a constant pressure in the pipeline 29. The impurities separated in the centrifuge are collected as the heaviest phase to form an outermost layer 31 in the sludge space of the centrifuge rotor and are discharged from there through openings (not shown) provided at the periphery of the rotor, either in the form of permanently open nozzles or in the form of normally closed openings which are intermittently opened, as by an axially movable, annular piston valve. It is possible to return to the centrifuge inlet 15, through a pipeline 32, a part of the living cell mass so that the latter then can be discharged with a desirably high concentration through the paring tube 28. This concentration can be adjusted at the start of the process and also during operation by means of a control valve 33 inserted in the return pipeline 32. When producing beer, a part of the carbonic acid may be discharged from the pressure side 34 of the pump 12 so as to be led through a pipeline 35 under superatmospheric pressure into the beer being discharged through the pipeline 23. The beer thus acquires a desired carbonic acid percentage, the magnitude of which can be controlled by means of a valve 36.

When starting the process, the plant is first filled with a mixture of water and cell mass already available through pipeline 1. After the centrifuge 16, by dehydration of the mixture, has increased its concentration of cell mass to a value necessary for the operation, wort at about 20° C is supplied through the pipeline 1. This wort gradually displaces the water in the mixture circulating in the plant, until the wort concentration has reached the value necessary for the operation. The diluted wort which has previously left the plant through the pipeline 23 can go to drain or be sent to a suitable place of consumption. In order to avoid sedimentation in the channels of the plant, a certain flow velocity of the mixture of wort and cell mass must be maintained. With a dry substance content of the mixture of 15 percent by weight, a velocity of 0.1 m/sec. is sufficient. If the dry substance content is below 10 percent by weight, flow velocities higher than 0.3 m/sec. are necessary. The channel system is so dimensioned that the holding time in it will be one to two hours, depending on the type of fermentation. The channel area should not be greater than 100 cm$^2$, if the flow through the channels is to take place in the form of a coherent plug. By adjusting the counter-pressure by means of the valve 30, it is possible to effect such a covering of the opening of the paring tube 28 that a suitable amount of air is mixed into the cell mass which is pumped out by the paring tube 28. When the paring tube opening is completely covered, air admixture into the cell mass is prevented, which may be desirable in certain types of alcohol fermentation. If production of cell mass is the main object of the present method, great amounts of air are sucked in by the paring tube 28. Excess of cell mass, which gives a corresponding pressure increase in the paring tube 28, is discharged by the valve 30. Due to the high concentration of living cells in the wort, the fermentation takes place rapidly. By means of the different helical heat exchangers provided in the fermentation channel, the temperature can be kept under the necessary control in the different parts of the channel. It is possible to effect not only cooling but also heat supply, if the desired fermentation course should require this. The different places for gas discharge, such as at 8 and 13, can be arranged to provide intervals of 10 minutes of reaction time along the channel. Furthermore, preferably at the inlets of the helical heat exchangers or the helical reactors, it is possible to make additions of nutritive salts and enzymes and also additions for controlling the pH value, whereby the fermentation conditions can be optimized in the different phases of the fermentation course.

EXAMPLES

1. Production of Beer

The plant is filled with beer yeast which has been stored since the preceding production. The yeast mass, which has a dry substance content of about 15 percent by weight, contains beer and wort and need not normally be concentrated before the start. If the yeast mass is contaminated, it is diluted with water and is allowed to pass through the centrifuge, the wash water being separated off and the channel system being filled with the cell mass. Wort of the desired composition and concentration, usually with an extract content of 8 to 16 percent by weight and a temperature of 10° to 15°C, is supplied to the circuit by means of the pump 2. The flow of the yeast mass is constant and has been adjusted by inserting suitable nozzles in the inner end of the tubes 25. The flow should be adjusted so that the holding time for a yeast cell will be 1 to 2 hours during the passage through the fermentation channel, which is sufficient at the high cell concentration involved here. A flow velocity of about 0.1 m/sec. is necessary when the dry substance content of the yeast mass is about 15 percent by weight. The wort quantity being supplied to the circuit is mixed effectively with the yeast mass in the mixer 3. Preferably, the ratio of wort to yeast mass should be 1:5 to 1:10. By varying the addition of wort, the holding time (fermentation time) can be varied within certain limits, whereas the main adjustment is made by means of the yeast flow from the centrifuge. During the fermentation, about 10 liters of carbonic acid are formed per one liter of wort, which gas must be discharged from the system, since the gas otherwise (due to its volume-occupying effect) reduces the contact time and thereby disturbs the fermentation course. Preferably, the channel is divided into sections, each corresponding to a contact time of 10 minutes, cooling (heat exchangers) and carbonic acid discharge being arranged for each section. Additions of chemicals, such as amino acids and enzymes, can be made during the passage through the channel, whereby the quality of the finished beer is controlled. Control of the fermentation course is carried out by measuring the specific gravity or the quantity of carbonic acid formed. In the centrifuge, the beer is separated in clarified state under superatmospheric pressure with a certain percentage of carbonic acid. Waste products formed, such as precipitated proteins and dead yeast cells, are separated off as a heavy phase. The yeast phase is discharged by means of a paring tube and is returned to the circuit. The yeast growth is controlled by means of the counter-pressure in the yeast outlet. The counter-pressure is proportional to the covering of the paring tube opening and inversely proportional to the air supply, whereby the yeast growth is controlled. Through the yeast growth, the pressure in the closed system increases, the valve 30 opening and giving off the excess yeast.

2. Production of Baker's Yeast

When producing baker's yeast, sterilized molasses (and nutritive salts) is usually used as substrate, the process being carried out mainly as in Example 1. The fermentation is aerobic, and for this reason the greatest possible quantity of air (or oxygen) must be supplied to the fermentation process in order to obtain a high yield. As has been mentioned earlier, air is supplied effectively in the centrifuge by means of the paring tubes for the yeast mass. The plant operates under superatmospheric pressure, great amounts of air dissolving in the suspension of molasses and yeast. Air or oxygen gas can also be added to other parts of the fermentation channel as well as nutritive salts, nitrogen gas, etc. After the mixture of molasses and yeast has passed a couple of holding sections, the air contaminated by gas development during this passage is sucked away and replaced by fresh air. The cell concentration in the suspension is also kept at a high level or at a dry substance content of about 15 percent by weight. Wash water may be added at the end of the fermentation channel and is then separated off in the centrifuge together with spent molasses. The formed yeast discharges automatically through the valve 30.

I claim:

1. In carrying out continuous fermentation in a wort substrate, the method which comprises feeding a flow of micro-organisms in a circuit including an elongated closed channel, continuously supplying wort to said circuit, subjecting the mixture of wort and micro-organisms to a centrifugal separating operation after fermentation has taken place in the circuit, thereby separating said mixture into three components, namely, fermented wort, a living cell mass and impurities, separately discharging said impurities component from the centrifugal separating operation, and continuously and separately discharging from the separating operation said fermented wort component and said living cell mass including living cells formed in said circuit.

2. The method of claim 1, in which the centrifugal separating operation provides said discharged living cell mass with a dry substance content of at least 10 percent by weight.

3. The method of claim 1, which comprises also controlling the cell growth in said circuit by supplying oxygen in a controlled amount to the living cell mass being discharged from said separating operation, a controlled mixture of oxygen-containing gas and living cell mass being discharged from said operation by a paring step.

4. The method of claim 1, which comprises also controlling the time of contact between the cell mass and the wort in said circuit by controlling the flow through said circuit.

5. The method of claim 1, which comprises also maintaining different temperatures in different parts of said closed channel by effecting indirect heat exchange between the flow through said channel and a heat exchange medium.

6. The method of claim 1 for the production of alcohol, which also comprises discharging carbonic acid from at least one point of the closed channel.

7. The method of claim 1, which also comprises controlling the fermentation by supplying an additive to said closed channel.

8. The method of claim 1, in which said fermentation is carried out under superatmospheric pressure.

* * * * *